United States Patent [19]

Kildal-Brandt et al.

[11] Patent Number: 5,126,952

[45] Date of Patent: Jun. 30, 1992

[54] BAR CODING CALIBRATION

[75] Inventors: Paul A. Kildal-Brandt, Webster; Thomas A. Weber, Rochester, both of N.Y.

[73] Assignee: Eastman Kodak Company, Rochester, N.Y.

[21] Appl. No.: 644,058

[22] Filed: Jan. 22, 1991

[51] Int. Cl.⁵ .......................................... G01N 37/00
[52] U.S. Cl. ............................... 364/571.02; 364/556; 364/571.04
[58] Field of Search .................... 364/571.01, 571.02, 364/571.03, 571.04, 571.05, 571.06, 571.07, 571.08, 556, 550, 554, 525; 235/462

[56] References Cited

U.S. PATENT DOCUMENTS 4,592,833  6/1986  Poppe et al. ........................ 422/56
4,884,213  11/1989  Iwata et al. ......................... 364/497

FOREIGN PATENT DOCUMENTS 60-93351  5/1985  Japan .
2129551  4/1983  United Kingdom .

OTHER PUBLICATIONS

"Principles of Calibration", Sec. 3 of E700 Operator's Manual (1985) Nov.
Directions, V. 6, No. 4 (1989) (month unknown).
Industrial Applications of Cubic Splines, Barosi, 1973, pp. 3-6.
"Splines & Statistics", Wegman et al, *J. of Amer. Stat. Assoc.*, vol. 78, No. 382, pp. 351-352 (1983)/Jun.

Primary Examiner—Parshotam S. Lall
Assistant Examiner—S. A. Melnick
Attorney, Agent, or Firm—Dana M. Schmidt

[57] ABSTRACT

There is described a method of barcoding data needed to determine a calibration curve for a test element in an analyzer. The process follows the steps of:

a) ascertaining by statistical analysis the ranges of values for R that are possible for three given concentration values $C_1$, $C_2$ and $C_3$, for a given assay, and assigning a high value H and a low value L for these ranges;

b) calculating for a given lot of the given assay, a calibration curve that correlates the analyzer response to the concentration, c) determining the analyzer response $R_1$, $R_2$ and $R_3$ from said calibration curve, that corresponds to the $C_1$, $C_2$ and $C_3$ values;

d) calculating the bar code value $B_i$ for $R_i$ of each of these $R_1$, $R_2$ and $R_3$ from the equation:

$$B_i = (10^n - 1)(R_i - L_i)/(H_i - L_i) \qquad (2)$$

where $R_i$ is $R_1$, $R_2$ or $R_3$, and $L_i$ and $H_i$ are the corresponding L and H values for that $R_i$;

e) rounding $B_i$ to the nearest integer; and f) supplying this value of $B_i$ for each of $R_i = R_1$, $R_2$ or $R_3$ in bar code form, using n-digit decimal numbers, so that only three sets of ($10^n$) possibilities are needed to accurately pass along data corresponding to the calibration coefficients even though each of the three coefficients can vary by more than that which can be specified using $10^n$ digits.

3 Claims, 2 Drawing Sheets

BAR CODING CALIBRATION

FIELD OF THE INVENTION

This invention relates to the field of methods for calibrating a clinical analyzer, and specifically to methods of passing on via a bar code the data needed to determine the calibration plot.

BACKGROUND OF THE INVENTION

It is conventional to calibrate a clinical analyzer for a given assay and a given lot of test elements using several known calibration liquids with known analyte concentration (or activity). These liquids are dispensed on test elements from that lot, and responses are determined. The determined responses and the known concentrations are then used to compute calibration coefficients, using a known equation, so that such coefficients and equation can be used to calculate unknown concentrations using the responses generated from patient samples, using the same lot of test elements. For example, in a glucose test, it is conventional to use the equation $$\text{Concentration} = A0 - A1 \cdot g1(\text{Response}) - A2 \cdot g2(\text{Response})^K \quad (1)$$

where g1 and g2 are cubic splines, K is an integer, usually = 2, and A0, A1 and A2 are specific calibration coefficients. (See the "Principles of Calibration" section from the E700 Operators Manual.) Equation (1) has been published in connection with the analyzers available from Eastman Kodak Company under the registered trademark of "Ektachem". For simplicity, g(R) is hereinafter referred to simply as "response", so that "R" is either the raw response or a cubic spline function of the raw response.

It is also known that such calibration coefficients could be predetermined at the factory in some instances, and passed on to the purchaser of a given lot of test elements for that assay, to avoid making the user recalibrate each time a new lot is shipped. Such information is passed on in a variety of ways.

The methods of passing on calibration information to the user include printed information and magnetic discs. Analyzers available from Eastman Kodak Company use a calibration diskette to transfer calibration information to users but the calibration coefficients are not included on this diskette. It is not economically feasible to send a calibration diskette with each lot of slides for each assay, so calibration coefficients are not sent to the customer via a diskette. Lot specific calibration coefficients can be transferred to the customer if the information is incorporated on the actual test element or its container. Two possible ways of transferring this information are by bar code or magnetic strip, as described in "Boehringer Mannheim detects high cholesterol with the Reflotron diagnostics system", *Directions*, Vol. 6, No. 4, fourth quarter, 1989, or in Japanese Kokai 60/93351. With single bar code strips and magnetic strips there is a limited number of digits, e.g., six, available to pass the calibration coefficients, yet the purchaser requires accurate values for the calibration coefficients A0, A1 and A2. If one is using a six decimal digit bar code, then A0, A1 and A2 must be passed to the purchaser using only six decimal digits. The obvious solution is to specify A0, A1 and A2 using two digits each. This means that each of these must be accurately specified by using the digits 0 to 99, the maximum possible in a 2-digit decimal finite number. Unfortunately, the specific solutions of A0, A1 and A2 can vary much more than this in a given assay, say glucose, because these coefficients are a function of the cubic splines that are used to best-fit the particular chemistry of a particular lot of test elements, to the data. Yet, bar coding is by far the preferred method of conveying the information of these coefficients, since that can be easily printed on each set of test elements or the package therefor. Nevertheless, it is well-recognized that a single strip of bar-coding is insufficient to portray the parameters of the calibration coefficients, as explained in Japanese Kokai 60/93351.

Of interest is the fact that the aforesaid '351 application attempts to solve the problem by providing, not a single strip of bar-coding, but rather, a triple strip of bar-coding, so as to allegedly increase the number of digits available to 1728 (12 cubed). However, this approach is unsatisfactory since it requires both a much larger label for triple the amount of codes, as well as a much more sophisticated bar code reader.

SUMMARY OF THE INVENTION

I have devised a method of determining the data for the bar code that solves the aforedescribed problems, while still using only a single bar code strip.

More specifically, there is provided a method of providing data in bar code form useful for the determination of the calibration curve of a lot of test elements in a clinical analyzer using a finite numbering system limited to n-digit decimal numbers, the curve having the mathematical formula $$C = a_0 - a_1 \cdot R - a_2 \cdot (R)^K, \quad (1)$$

where C is the predicted concentration of a sample liquid analyzed by the analyzer, R is the response actually measured in the analyzer or cubic spline function of that response, K is a coefficient assigned to the analyzer, and $a_0$, $a_1$ and $a_2$ are the calibration coefficients and which can vary well beyond that which can be specified using $(10^n)$ digits. The method comprises the steps of a) ascertaining by statistical analysis the ranges of values for R that are possible for three given concentration values $C_1$, $C_2$ and $C_3$, for a given assay, and assigning a high value H and a low value L for these ranges;

b) calculating for a given lot of the given assay a calibration curve that correlates the analyzer response to the concentration;

c) determining the analyzer response $R_1$, $R_2$ and $R_3$ from the calibration curve, that corresponds to the $C_1$, $C_2$ and $C_3$ values;

d) calculating the bar code value $B_i$ for $R_i$ of each of these $R_1$, $R_2$ and $R_3$ from the equation $$B_i = (10^n - 1)(R_i - L_i)/(H_i - L_i) \quad (2)$$

where $R_i$ is $R_1$, $R_2$ or $R_3$, and $L_i$ and $H_i$ are the corresponding L and H values for that $R_i$;

e) rounding $B_i$ to the nearest integer; and f) supplying this value of $B_i$ for each of $R_i = R_1$, $R_2$ or $R_3$ in bar code form, so that only three sets of $(10^n)$ possibilities are needed to accurately pass along data corresponding to the calibration coefficients even though each of the three coefficients can vary by more than that which can be specified using $10^n$ digits.

Accordingly, it is an advantageous feature of the invention that a single bar code strip of only a few digits can be accurately provided with the data needed to pass on a calibration curve for a given lot of test elements, to the user.

It is a related advantageous feature of the invention that a simplified bar code, and hence a simplified bar code reader, can be used to represent the data needed to calibrate for lot-specific calibration parameters.

Other advantageous features will become apparent upon reference to the detailed Description of the Preferred Embodiments, when read in light of the attached drawings.

DESCRIPTION OF THE PREFERRED EMBODIMENTS

The invention is hereinafter described in connection with the preferred embodiments, which use a preferred bar code on preferred dried, slide test elements in a preferred clinical analyzer. In addition, the invention is useful regardless of the form of the bar code, regardless of the format or assay of the test element (or its cartridge) on which the code is placed, and regardless of the analyzer in which the test element is tested. However, the invention is most useful in a single strip bar code.

Any bar code design is useful with this invention, provided that at least six digits are available, that is, 3 pairs, to provide three numbers that can range from 0 to 99. A particularly well-known form that provides this capability is the so-called "interleaved two of 5".

The preferred test elements are the slide test elements available from Eastman Kodak Company under the trademark "Ektachem" slides, or from Fuji Photo Film Co. under the tradename "Drychem" slides.

The preferred analyzers are any of the analyzers available from Eastman Kodak Company under the trademark "Ektachem" analyzer, or from Fuji Photo Film Co. under the tradename "5000".

Figure 1:
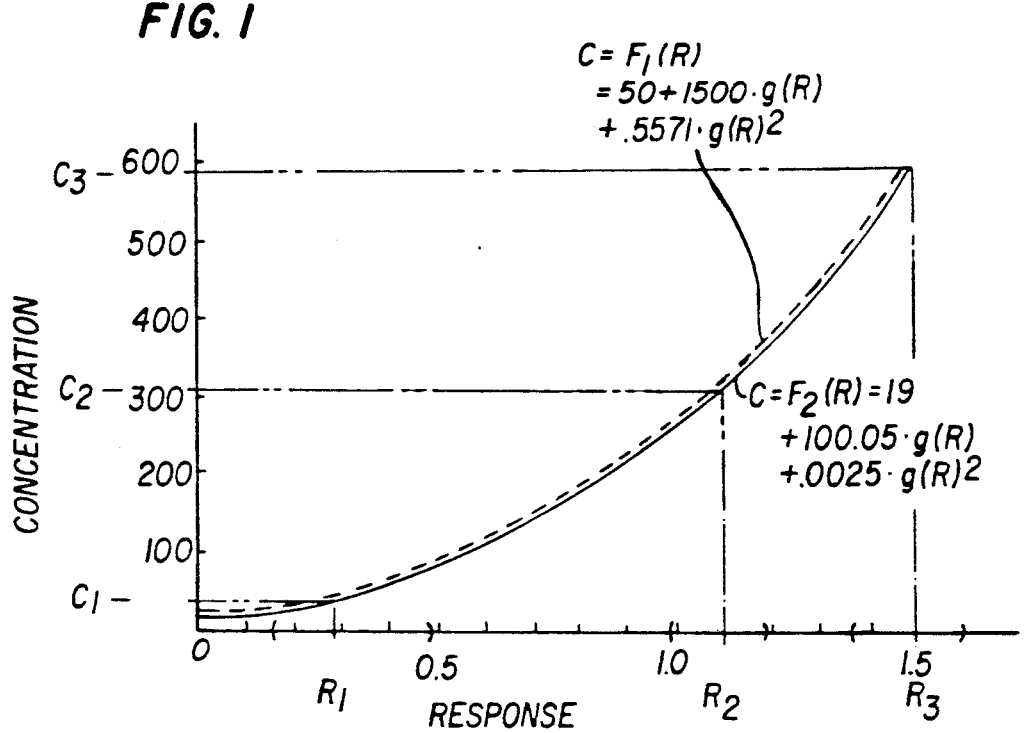
FIG. 1 is a calibration plot of the expected concentrations for a given response in an analyzer for a given assay, demonstrating both the problem and the solution.

Referring to FIG. 1, a representative plot is shown of a useful calibration curve, for example, for glucose. In such plots, the expected concentration C is plotted versus the response R measured on the analyzer, where R can be the raw response or a g(R) which is a cubic spline of the raw response. In general, the raw response can be any of reflectance, optical density obtained from reflectance, rate of change of these responses, or an electrical potential created by a differential measurement of ion concentration in two ion-selective electrodes. For glucose, the raw response is either in reflectance or optical density $D_R$, where $D_R = \log(1/\text{reflectance})$. The curve can be expressed as concentration $C = A_0 + A_1 \cdot \text{Response} + A_2 \cdot \text{Response}^K$, K usually being a value of 2.

The two plots, one a solid line and one a dashed line, both represent a good fit to the data that can be obtained on a given lot of test elements for this assay. That is, both curves occupy approximately the same space. However, the values of the coefficients $A_0$, $A_1$ and $A_2$ are drastically different for the two curves, as shown, where the response is optical density as determined by the analyzer. These values were determined as follows:

If one assumes the concentration C for 3 calibrators of different levels is 39, 309, and 596 mg/dL, as shown in FIG. 1, and a corresponding response of 0.28, 1.1 and 1.5 Dr respectively, it is possible to solve for $A_0$, $A_1$ and $A_2$ in the three linear equations (I), (II) and (III):

$$39 = A_0 + A_1 \cdot g_1(0.28) + A_2 \cdot g_2(0.28)^K \qquad (I)$$

$$309 = A_0 + A_1 \cdot g_1(1.1) + A_2 \cdot g_2(1.1)^K \qquad (II)$$

$$596 = A_0 + A_1 \cdot g_1(1.5) + A_2 \cdot g_2(1.5)^K \qquad (III)$$

A useful method for evaluating splines is to use the spline parameters X, Y and F"(x), where F"(x) is the second derivative of the function at that x value, as described in *Industrial Applications of Cubic Spline Functions*, by N. J. Barosi, Oct. 26, 1973, pp. 3–6 (A Presentation to the 17th Annual Technical Conference of the American Society for Quality Control and the American Statistical Association), and "Splines and Statistics", by Edward J. Wegman and Ian W. Wright, *Journal of the American Statistical Association*, June 1983, Volume 78, Number 382, Theory and Methods Section, pp. 351–352.

COMPARATIVE EXAMPLE 1

Letting K = 2 and assuming the following spline parameters, where $g_1 = g_2$:

| X | Y | F"(x) |
| --- | --- | --- |
| −.1 | .0107 | 0 |
| .15 | .2484 | 0 |
| .3 | .4155 | 6.54 |
| .7 | 1.422 | 3.05 |
| 1.2 | 3.633 | 6.65 |
| 1.4 | 5.012 | 20.17 |
| 2 | 12.51 | 0 | one finds that $A_0$, $A_1$ and $A_2 = 19$, 100.05 and 0.0025. See, e.g., FIG. 1 for a curve representing these values (the solid line).

Predicting the densities 0.2, 0.4, 0.6, 0.8, 1.2, 1.4, 1.6, and 1.8 using these calibration coefficients, splines, and K-value one obtains concentrations: 30, 59, 111, 178, 260, 364, 502, 707, and 966.

COMPARATIVE EXAMPLE 2

If one changes the spline parameters so that they are

| X | Y | F"(x) |
| --- | --- | --- |
| −.1 | −.0325 | 0 |
| .15 | −.0166 | 0 |
| .3 | −.0055 | .436 |
| .7 | .0617 | .203 |
| 1.2 | .2091 | .444 |
| 1.4 | .3011 | 1.35 |
| 2 | .8014 | 0 | one finds that $A_0$, $A_1$ and $A_2 = 50$, 1500 and 0.5571, respectively. This is the dashed curve of FIG. 1.

Predicting the densities 0.2, 0.4, 0.6, 0.8, 1, 1.2, 1.4, 1.6, and 1.8 using these calibration coefficients, splines, and K-value the obtains concentrations: 30, 59, 111, 178, 260, 364, 502, 707, and 966. Thus the splines in Comparative Example 1 and Comparative Example 2 produce dramatically different calibration parameters $A_0$, $A_1$ and $A_2$, yet define the identical density-to-concentration relationship. Thus, coefficient $A_1$ for one curve is 1500, but for the other curve is 100.05. Clearly, any attempt to confine such variances of $A_1$ to two digits of from 0 to 99 in value is doomed to failure, in terms of accuracy. Similar problems exist for bar-coding the variances obtainable just from these curves, for $A_0$ and $A_2$.

Still further, accuracy problems exist in bar coding the $a_0$, $a_1$ and $a_2$ coefficients. This is illustrated in an additional Comparative Example which follows the description of the preferred embodiments.

Figure 2:
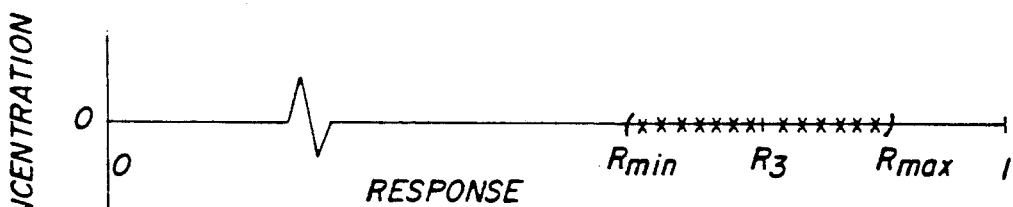
FIG. 2 is an enlarged, fragmentary plot of just the abscissa axis of FIG. 1, to further clarify the invention.

In accordance with the invention, instead of trying to fit the drastically varying $a_0$, $a_1$ and $a_2$ coefficients (of which $A_0$, $A_1$ and $A_2$ noted above are specific examples) into the bar code, the solution is to fit the variances in the response R into the bar code. Such variances are in fact much less, as shown by the parenthesis around $R_i$ in FIGS. 1 and 2. The following non-exhaustive example illustrates the practice of the invention.

EXAMPLE 1

Glucose

The optical densities (Dr) associated with glucose concentrations of 40, 150 and 550 mg/dl were found for five different generations of glucose slides. Data on 21 different coatings were found, using an "Ektachem 700" analyzer. The mean and standard deviation of the Drs at the glucose concentrations were:

TABLE I

| Concentration | Mean Dr | Standard Deviation (S.D.) |
|---|---|---|
| 40 | .3122 | .0594 |
| 150 | .7340 | .0411 |
| 550 | 1.4765 | .0381 |

It can be shown, for a given concentration, that the Dr on a new coating will fall, in 99% of the cases, within the interval [Mean $- 3 \times$ S.D., Mean $+ 3 \times$ S.D.]. Thus, for the three fixed concentrations, new coatings must have Drs for these concentrations which fall in the ranges:

TABLE II

| Concentration | Low Dr Range (L) | High Dr. Range (H) |
|---|---|---|
| 40 | .1399 | .4905 |
| 150 | .6106 | .8574 |
| 550 | 1.3623 | 1.5908 |

Therefore, for the equation (2) noted above, it is these values of H and L that are used to calculate what each $B_i$ should be for a given Dr response at a given concentration C. More specifically, given a lot of slides, a glucose concentration C of 150 mg/dl produces a Dr of 0.7969 on one of the elements of the lot. It is this number that is to be approximated using a two digit barcode. Using the Dr ranges in Table II it is clear that the response of a fluid with a concentration of 150 mg/dl must lie in the interval [0.6106, 0.8574]. Thus, the barcode value $B_2$ is $$B_2 = 99\,((0.7969 - 0.6106)/(0.8574 - 0.6106)) \sim 75$$

(from equation (2)). The approximate value found when the barcode is converted back by a customer using again an "Ektachem 700" analyzer is:

$$R_2 \text{ (Converted)} = 0.6106 + (75(0.8574 - 0.6106))/99 = 0.7976$$

These converted values of $R_1$, $R_2$ and $R_3$ are processed by the analyzer to create a new calibration curve using three sets of equations similar to equations (I), (II) and (III) above. In this case of $R_2$, an error of only 0.0007 was induced by creating and converting the barcode.

If one assumes that concentrations of 40 and 550 mg/dl produce Drs of 0.4587 and 1.3706, this combination of concentrations and Drs, including a Dr of 0.7969 at 150 mg/dl, produce a true calibration curve with calibration coefficients of:

$$-27.475, 88.737 \text{ and } 6.764,$$

using the spline of Comparative Example 1 above and a K = 2. Now, $$B_1 = 99((.4587 - .1399)/(.4905 - .1399)) = 90.02 \sim 90$$
(from equation 2)

$$B_3 = 99((1.3706 - 1.3623)/(1.5908 - 1.3623)) = 3.60 \sim 4$$
(from equation 2)

and therefore, $$R_1 \text{ (converted)} = .1399 + ((90(.4905 - .1399))/99 = .4586$$
$$R_3 \text{ (converted)} = 1.3623 + ((4(1.5908 - 1.3623))/99 = 1.3715$$

Calibrating with concentrations of 40, 150 and 550 mg/dl and the converted densities of 0.4586, 0.7976, and 1.3715 one obtains the "converted" calibration coefficients:

$$-27.227, 88.422 \text{ and } 6.771.$$

From these, a new curve is drawn and the densities corresponding to the "true" concentrations set forth in Table III that follows, can be used to predict a "converted concentration". The difference between the "true" concentration and the "predicted" concentration using the "converted response" shows the error which would result from passing the above true calibration curve using the bar code that carries the response value.

TABLE III

| True Concentration | Predicted Concentration Using Converted Responses | Absolute Bias |
|---|---|---|
| 30 | 30.06 | .06 |
| 61 | 60.96 | −.04 |
| 92 | 91.87 | −.13 |
| 123 | 122.79 | −.21 |
| 154 | 153.7 | −.30 |
| 185 | 184.03 | −.37 |
| 216 | 215.55 | −.45 |
| 247 | 246.48 | −.52 |
| 278 | 277.41 | −.59 |
| 309 | 308.35 | −.65 |
| 340 | 339.28 | −.72 |
| 371 | 370.22 | −.78 |
| 402 | 401.16 | −.84 |
| 433 | 432.11 | −.89 |
| 464 | 463.05 | −.95 |
| 495 | 494 | −1.00 |
| 526 | 524.94 | −1.06 |
| 557 | 555.89 | −1.11 |

TABLE III-continued

| True Concentration | Predicted Concentration Using Converted Responses | Absolute Bias |
|---|---|---|
| 588 | 586.84 | −1.16 |
| 619 | 617.8 | −1.20 |
| 650 | 648.75 | −1.25 |

Figure 5:
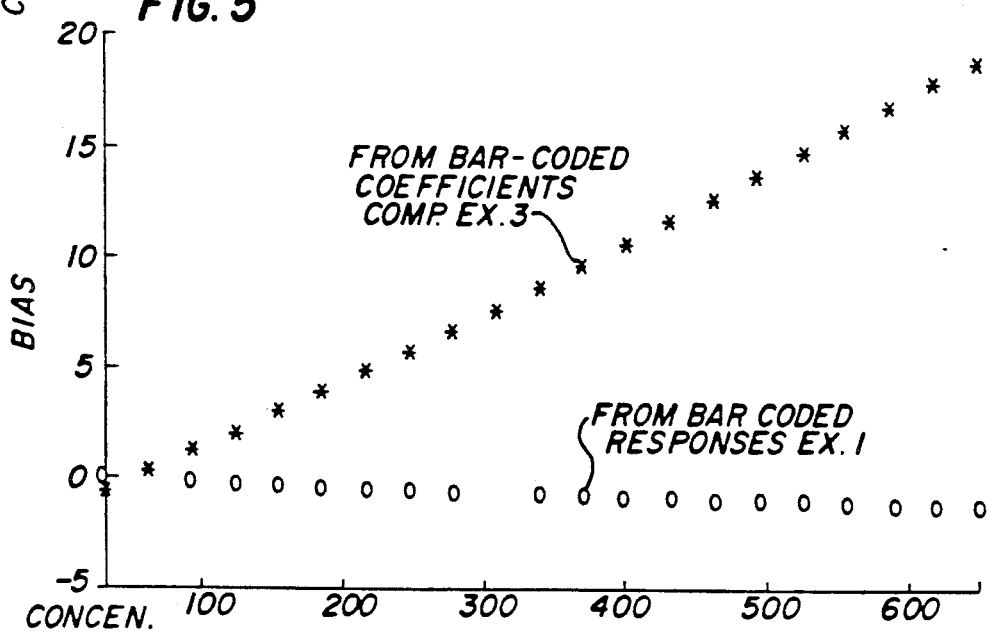
FIG. 5 is a graphical representation of the differences which exist between the two methods shown in the examples.

Such biases are negligible, as is seen in FIG. 5.

Although this example shows an "E700" analyzer being used both to create the bar code, and to adjust the calibration curve at the customer site, that need not be the case. That is, the site analyzer can be slightly different from the one used to create the bar code, so long as the calibration math is substantially the same for both types of analyzers. Thus, the bar code created on the "E700" analyzer can be used at a customer site that has an "E400" or "E500" analyzer, for example.

EXAMPLE 2

BUN

The optical densities (Dr) associated with BUN concentrations of 10, 40 and 120 mg/dl were found for two different generations of BUN slides. Data on 16 different coatings were found using an "Ektachem E700". The mean and standard deviation of the Drs at the BUN concentrations were:

TABLE IV

| Concentration | Mean Dr | Standard Deviation (S.D.) |
|---|---|---|
| 10 | .3608 | .0231 |
| 40 | .7958 | .0278 |
| 120 | 1.8725 | .0755 |

It can be shown, for a given concentration, that Dr on a new coating will fall within the interval [Mean −3 · S.D., Mean −3 · S.D.]. Thus, for the three fixed concentrations, new coatings must have Drs for these concentrations which fall in the ranges:

TABLE V

| Concentration | Low Dr Range (L) | High Dr Range (H) |
|---|---|---|
| 10 | .2915 | .4301 |
| 40 | .7124 | .8792 |
| 120 | 1.6458 | 2.0991 |

Therefore, for the equation (2) noted above, it is these values of H and L that are used to calculate what each $B_i$ should be for a given Dr response at a given concentration C. More specifically, given a lot of slides, a BUN concentration of C of 10 mg/dl corresponds to a Dr of 0.3756 on one of the elements of the lot. It is this number that is to be approximated using a two digit bar code. Using the Dr ranges in Table V it is clear that the response of a fluid with a concentration of 10 mg/dl must lie in the interval [0.2915, 0.4301]. Thus the bar code value $B_1$ is $$B_1 = 99 ((0.3756 - 0.2915)/(0.4301 - 0.2915)) = 60$$

(from equation 2). The approximate value found when the bar code is converted back by a customer using again an "Ektachem 700" analyzer is:

$$R_1(\text{converted}) = 0.2915 + ((60(0.4301 - 0.2915))/99) = 0.3755.$$

In this case, an error of only 0.0001 was induced by creating and converting the bar code (an error of only 0.03%).

It will be appreciated from the foregoing examples that the bar-coding of the particular response $R_i$ as a fraction of (H-L) for given values of $C_1$, $C_2$ and $c_3$, acts to bypass a passing on of the coefficients $A_0$, $A_1$ and $A_2$. $A_0$, $A_1$ and $A_2$ are instead recomputed in the analyzer using the $R_i$ and $C_i$ as described above.

COMPARATIVE EXAMPLE 3

Barcoding Calibration Parameters $a_0$, $a_1$ and $a_2$

Figure 3:
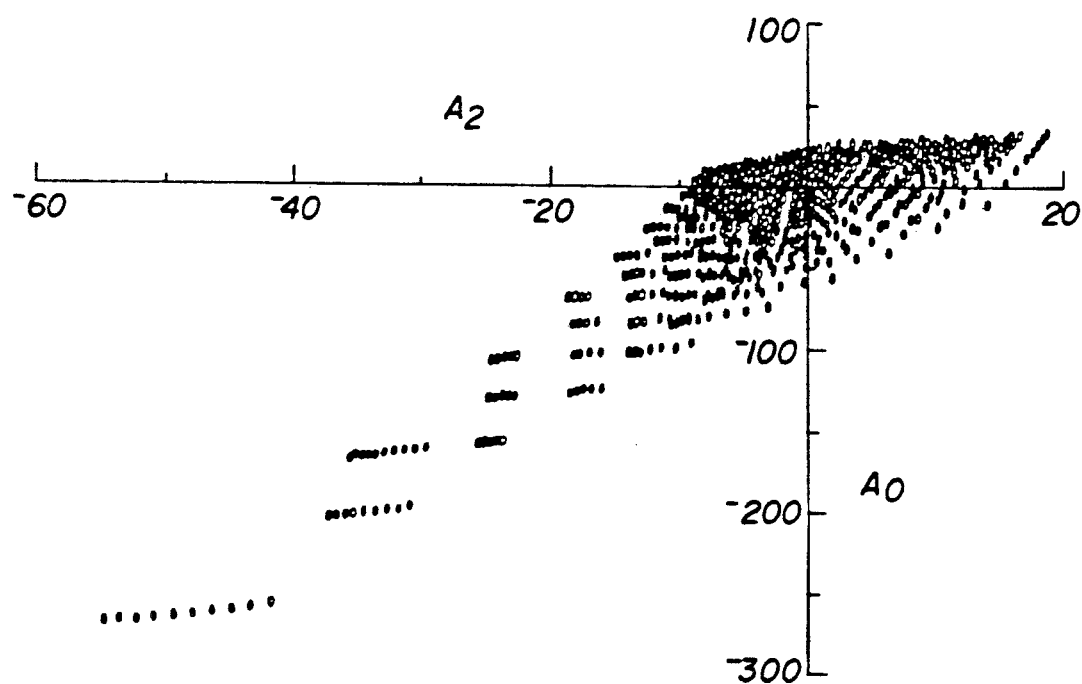
FIGS. 3 and 4 are two-dimensional plots of a three-dimensional space of the possible values for the calibration coefficients $A_0$, $A_1$ and $A_2$ for the curves of FIG. 1.
Figure 4:
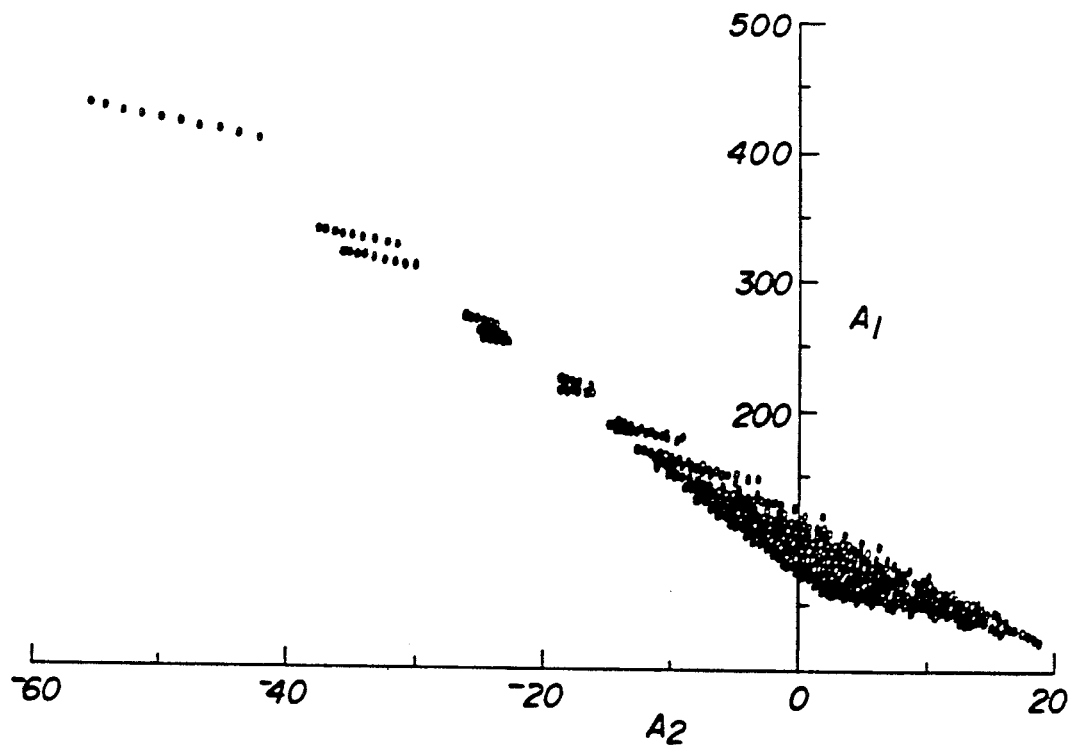

FIGS. 3 and 4 indicate another weakness in specifying calibration parameters rather than test element responses. In this study the following simulation was performed:

Step 1) For each of the glucose concentrations in Table II, i.e., 40, 150 and 550, the range listed was partitioned into ten evenly spaced densities which spanned the known density ranges for the concentration. The resulting densities for the given concentrations are listed in the Table VI below.

TABLE VI

| 40 mg/dl | 150 mg/dl | 5550 mg/dl |
|---|---|---|
| .1399 | .6106 | 1.3623 |
| .1789 | .6380 | 1.3877 |
| .2187 | .6654 | 1.4131 |
| .2568 | .6929 | 1.4385 |
| .2957 | .7203 | 1.4639 |
| .3347 | .7477 | 1.4892 |
| .3736 | .7751 | 1.5146 |
| .4126 | .8026 | 1.5400 |
| .4515 | .8300 | 1.5654 |
| .4905 | .8574 | 1.5908 |

Step 2) K was set equal to 2 and $g_1 = g_2 =$ glucose spline from Comparative Example 1 above.

Step 3) All possible combinations of densities from table 5 were found where one density was chosen from each column. This resulted in one thousand sets of three densities.

Step 4) One thousand calibrations were performed using the glucose concentrations 40, 150 and 550 mg/dl and each set of densities found in step 3.

Step 5) The one thousand sets of calibration parameters $A_0$, $A_1$ and $A_2$ generated in Step 4 were recorded.

Step 6) $A_0$ vs $A_2$ from each calibration parameter set found in Step 5, was plotted in FIG. 3, and $A_1$ vs $A_2$, from each calibration parameter set found in Step 5, was plotted in FIG. 4. (Plotting all three parameters at the same time would require creating a three dimensional plot.)

Now, if one attempted to bar code $A_0$, $A_1$ and $A_2$ rather than the test element responses, one would need to specify three ranges using the same format as in table II for $A_0$, $A_1$ and $A_2$. These ranges would be similar to the ones listed in table VII below, determined from FIGS. 3 and 4:

TABLE VII

| $A_0$, $A_1$, $A_2$ | Low Range | High Range |
|---|---|---|
| $A_0$ | −300 | 100 |
| $A_1$ | 0 | 500 |
| $A_2$ | −60 | 20 |

When bar coding the True Calibration Coefficients (i.e., −27.475, 88.737, and 6.764) found above using Table VII, one obtains:

$$B_1 = 99((-27.475 - 300)/(100 - 300)) = 67.45 \sim 67$$

$$B_2 = 99((88.737 - 0)/(500 - 0)) = 17.57 \sim 18$$

$$B_3 = 99((6.764 - 60)/(20 - 60)) = 82.62 \sim 83$$

Converting the bar code back to calibration coefficients one finds:

$$A_0 \text{(converted)} = -300 - (67(100 - 300))/99 = -29.293$$

$$A_1 \text{(converted)} = 0 - (18(500 - 0))/99 = 90.909$$

$$A_2 \text{(converted)} = -60 - (83(20 = 60))/99 = 7.071$$

Thus, the Converted Cal. Coef. = $-29.293$, $90.909$, and $7.071$.

Table VIII below shows the error in predicted concentration which would result from passing the true calibration curve using calibration coefficients on the bar code, rather than the responses as per the invention.

TABLE VIII

| True Concentration | Predicted Concentration Using Converted Responses | Absolute Bias |
|---|---|---|
| 30 | 29.64 | −.36 |
| 61 | 61.47 | .47 |
| 92 | 93.32 | 1.32 |
| 123 | 125.19 | 2.19 |
| 154 | 157.08 | 3.08 |
| 185 | 188.99 | 3.99 |
| 216 | 220.91 | 4.91 |
| 247 | 252.84 | 5.84 |
| 278 | 284.79 | 6.79 |
| 309 | 316.75 | 7.75 |
| 340 | 348.72 | 8.72 |
| 371 | 380.70 | 9.70 |
| 402 | 412.70 | 10.70 |
| 433 | 444.69 | 11.69 |
| 464 | 476.70 | 12.70 |
| 495 | 508.72 | 13.72 |
| 526 | 540.74 | 14.74 |
| 557 | 572.77 | 15.77 |
| 588 | 604.81 | 16.81 |
| 619 | 636.85 | 17.85 |
| 650 | 668.90 | 18.90 |

FIG. 5 is a graphical representation of the differences which exist between the two methods for this example. It uses the data found in tables III and VIII. (The ordinate value of zero represents "truth".) A comparison of table III and table VIII shows that passing responses on the bar code results in a significantly better approximation of the true calibration curve than the calibration curve found by passing calibration coefficients directly on the bar code.

The invention has been described in detail with particular reference to certain preferred embodiments thereof, but it will be understood that variations and modifications can be effected within the spirit and scope of the invention.

What is claimed is:

1. A method of providing data in bar code form useful for the determination of the calibration curve of a lot of test elements in a clinical analyzer using a finite numbering system limited to n-digit decimal numbers, said curve having the mathematical formula $$C = a_0 - a_1 \cdot R - a_2 \cdot (R)^K \tag{1}$$

where C is the predicted concentration of a sample liquid analyzed by the analyzer, R is the response actually measured in the analyzer or a cubic spline function of that response, K is a coefficient assigned to the analyzer, and $a_0$, $a_1$ and $a_2$ are said calibration coefficients which can vary beyond that which can be specified using ($10^n$) digits; the method comprising the steps of:
   a) ascertaining by statistical analysis the ranges of values for R that are possible for three given concentration values $C_1$, $C_2$ and $C_3$, for a given assay, and assigning a high value H and a low value L for these ranges;
   b) calculating for a given lot of the given assay, a calibration curve that correlates the analyzer response to the concentration;
   c) determining the analyzer response $R_1$, $R_2$ and $R_3$ from said calibration curve, that corresponds to said $C_1$, $C_2$ and $C_3$ values;
   d) calculating the bar code value $B_i$ for $R_i$ of each of these $R_1$, $R_2$ and $R_3$ from the equation $$B_i = (10^n - 1)(R_i - L_i)/(H_i - L_i) \tag{2}$$

where $R_i$ is $R_1$, $R_2$ or $R_3$, and $L_i$ and $H_i$ are the corresponding L and H values for that $R_i$;
   e) rounding $B_i$ to the nearest integer; and
   f) supplying this value of $B_i$ for each of $R_i = R_1$, $R_2$ or $R_3$ in bar code form, so that only three sets of ($10^n$) possibilities are needed to accurately pass along data corresponding to said calibration coefficients even though each of said three coefficients can vary by more than that which can be specified using $10^n$ digits.

2. A method as defined in claim 1, and further including the step of converting said supplied $B_i$ values of step e) into actual values of $R_1$, $R_2$ and $R_3$, by solving equation (1) for $R_i$, given the stored values of $B_i$.

3. A method of providing data as defined in claims 1 or 2, wherein $n = 2$, and said step a) includes the steps of determining the mean value M to be expected in all test elements for said given assay and the standard deviation SD from the mean, and assigning as value H the value $M + 3 \times Sd$, and as value L the value $M - 3 \times SD$, for a given value of $C_1$, $C_2$ and $C_3$.

* * * * *

UNITED STATES PATENT AND TRADEMARK OFFICE

CERTIFICATE OF CORRECTION

Patent No.: 5,126,952

Dated: June 30, 1992

Inventors: Paul A. Kildal-Brandt and Thomas A. Weber

It is certified that error appears in the above-identified patent and that said Letters Patent is hereby corrected as shown below:

Column 9, line 2, should read:

$$--B_1 = 99((-27.475 + 300)/(100 + 300)) = 67.45 \sim 67--$$

Column 9, line 6, should read:

$$--B_3 = 99((6.764 + 60) / (20 + 60)) = 82.62 \sim 83--$$

Signed and Sealed this

Thirty-first Day of August, 1993

Attest:

BRUCE LEHMAN

*Attesting Officer*     *Commissioner of Patents and Trademarks*